US007438192B1

(12) United States Patent  
Kohler et al.

(10) Patent No.: US 7,438,192 B1  
(45) Date of Patent: Oct. 21, 2008

(54) ELECTRONIC CONTROL SYSTEM FOR CONTAINER INDEXING AND INSPECTION APPARATUS

(75) Inventors: Timothy A. Kohler, Waterville, OH (US); William R. Martin, Slippery Rock, PA (US); Timothy McIntosh, Pittsburgh, PA (US); Gregory A. Ritz, Berkey, OH (US); Noel D. Wendt, Toledo, OH (US)

(73) Assignee: Owens-Brockway Glass Container Inc., Perrysburg, OH (US)

( * ) Notice: Subject to any disclaimer, the term of this patent is extended or adjusted under 35 U.S.C. 154(b) by 534 days.

(21) Appl. No.: 10/856,515

(22) Filed: May 28, 2004

(51) Int. Cl.  
*B07C 5/00* (2006.01)

(52) U.S. Cl. .................................................. 209/523

(58) Field of Classification Search ............. 198/470.1, 198/474.1, 376, 377.07, 379; 264/538; 209/523  
See application file for complete search history.

(56) References Cited

U.S. PATENT DOCUMENTS

| | | | | |
|---|---|---|---|---|
| 2,682,802 | A | * | 7/1954 | Fedorchak et al. .......... 356/428 |
| 3,313,409 | A | | 4/1967 | Johnson |
| 3,880,750 | A | * | 4/1975 | Butler et al. ................. 209/526 |
| 4,046,258 | A | * | 9/1977 | Damm ........................ 209/524 |
| 4,084,686 | A | | 4/1978 | Calhoun |
| 4,239,116 | A | | 12/1980 | Eisenberg et al. |
| 4,378,493 | A | * | 3/1983 | Dorf et al. ............... 250/223 B |
| 4,378,495 | A | * | 3/1983 | Miller ..................... 250/223 B |
| 4,433,785 | A | | 2/1984 | Riggs et al. |
| 4,584,469 | A | * | 4/1986 | Lovalenti ................ 250/223 B |
| 4,644,151 | A | * | 2/1987 | Juvinall ................... 250/223 B |
| 4,651,879 | A | | 3/1987 | Harris et al. |
| 4,852,415 | A | * | 8/1989 | Bogatzki et al. ........... 73/865.8 |
| 5,183,145 | A | | 2/1993 | Williams et al. |
| 5,231,926 | A | | 8/1993 | Williams et al. |
| 5,233,186 | A | * | 8/1993 | Ringlien ................. 250/223 B |
| 5,291,271 | A | * | 3/1994 | Juvinall et al. ............. 356/632 |
| 5,414,939 | A | * | 5/1995 | Waugaman ................... 33/522 |
| 5,558,233 | A | | 9/1996 | Dimmick et al. |
| 5,637,864 | A | * | 6/1997 | Nicks et al. ............. 250/223 B |
| 5,718,323 | A | | 2/1998 | Flix |
| 5,896,195 | A | * | 4/1999 | Juvinall et al. ........... 356/240.1 |
| 6,172,355 | B1 | | 1/2001 | Gast et al. |
| 6,264,457 | B1 | | 7/2001 | Ohmes et al. |
| 6,435,336 | B1 | | 8/2002 | Knodler |
| 6,557,695 | B2 | * | 5/2003 | Gerber et al. ............ 198/473.1 |
| 6,581,751 | B1 | | 6/2003 | Nickey et al. |
| 6,745,890 | B2 | * | 6/2004 | Nickey et al. .............. 198/379 |
| 6,848,564 | B2 | * | 2/2005 | Nickey et al. .............. 198/379 |
| 2003/0034227 | A1 | | 2/2003 | Gerber et al. |

* cited by examiner

*Primary Examiner*—Mark A Deuble

(57) ABSTRACT

A glassware inspection apparatus that includes an electronic control system and method for optimum control of indexing and inspecting glass containers. The control system generally includes a driver circuit for each servo motor of the apparatus, an electronic control unit, and an operator interface. Information about the apparatus and the particular containers being inspected is entered into the control system through the operator interface. The electronic control unit executes a recursive algorithm that utilizes the inputted information, as well as predetermined constraints of the apparatus, to develop an optimum motion profile for each servo motor. The optimum motion profiles provide the overall apparatus with coordinated control and increased container throughput speed, while efficiently distributing cycle time and thermal energy between the various servo motors.

21 Claims, 6 Drawing Sheets

- - - Spring Finger Assembly
—— Fixed Finger Assembly

US 7,438,192 B1

ELECTRONIC CONTROL SYSTEM FOR CONTAINER INDEXING AND INSPECTION APPARATUS

FIELD OF THE INVENTION

The present invention generally relates to the indexing and inspection of glass articles such as glass containers, and more particularly to an electronic control system and method for controlling servo motors that are a part of an indexing and inspection apparatus.

BACKGROUND OF THE INVENTION

In the manufacture of glassware, such as glass containers, various anomalies or variations can occur that affect the commercial acceptability of the containers. These anomalies, termed "commercial variations," can involve dimensional characteristics of the container such as at the container finish, surface characteristics that can affect acceptable operation of the container such as surface variations at the container sealing surface, or variations such as stones or checks within the container finish, sidewall or bottom, to name but a few. Furthermore, it is conventional practice to mold indicia on each container that are indicative of the mold of origin of the container for inspection and quality control purposes.

U.S. Pat. No. 4,378,493 illustrates a starwheel-type conveyor for accepting containers in sequence from an infeed conveyor and transporting the containers through a series of inspection stations. At least some of the inspection stations hold the containers in position and rotate them about their central axes such that they may electro-optically inspect the containers for commercial variations and/or mold codes. The term "inspection" is used in its broadest sense to encompass any optical, electro-optical, mechanical or electrical observation or engagement with the container to measure or determine a potentially variable characteristic, including but not necessarily limited to mold codes and commercial variations.

U.S. Pat. No. 6,581,751 B1 discloses a method and apparatus for indexing glassware through a series of angularly spaced inspection stations, and includes first and second arrays of glassware gripping fingers mounted on rotatable carriers. The carriers rotate around a common axis, and are each driven by a servo motor. The carriers are designed such that at least one of the carriers rotates with respect to the other when the gripping fingers are either to grip or release an article of glassware, and they are designed to rotate in unison when they are to index an article of glassware from station to station.

The above-noted patents illustrate examples of some of the many devices that may be employed in the glassware inspection field, as numerous other examples also exist. For instance, U.S. Pat. Nos. 2,682,802, 3,880,750, 4,046,258, 4,378,493, 4,378,495, 4,584,469, 4,644,151, 5,233,186, 5,291,271, 5,414,939, 5,637,864, 5,896,195, and European Patent Nos. 0961113 and 0764846 each disclose methods and/or devices that may also be employed for the purpose of inspecting containers, including optical, electrical and mechanical inspection.

SUMMARY OF THE INVENTION

The present invention includes a number of aspects, which can be implemented separately from or, more preferably, in combination with each other. Some of these aspects pertain to apparatuses while some pertain to methods.

A control system is provided for use with a container indexing and inspection apparatus generally including a first driver circuit for controlling a first servo motor and a second driver circuit for controlling a second servo motor. The control system controls the first and second driver circuits such that they respectively drive the first and second servo motors at optimum speeds. The optimum speeds are determined by utilizing at least one physical parameter of the container being indexed and inspected.

An apparatus for inspecting containers generally including a carrier device coupled to at least one first servo motor, a roller device coupled to a second servo motor, and means for determining the optimum speeds for each of the servo motors based upon one or more physical parameters associated with the container and the motion characteristics of the other motions.

A method is provided for controlling the movement of containers through an inspection apparatus. The method generally includes the following steps: (a) providing a first servo motor, (b) providing a second servo motor, (c) providing an electronic control system, (d) inputting information into the control system, where the information includes at least one physical parameter of the container, (e) determining optimum motion profiles for the servo motors based at least in part upon the container physical parameter, and (f) driving the servo motors according to the optimum motion profiles.

A method also is provided for determining an optimum motion profile for use with a servo motor. The method generally includes the following steps: (a) providing a container indexing and inspection apparatus, (b) providing an electronic control system, (c) entering information into the control system, wherein the information includes at least one physical parameter of a container being inspected by the apparatus, and (d) causing the electronic control system to execute a recursive algorithm that determines an optimum motion profile by utilizing the container physical parameter.

BRIEF DESCRIPTION OF THE DRAWINGS

The invention, together with additional objects, features, advantages and aspects thereof, will be best understood from the following description, the appended claims and the accompanying drawings in which:

DETAILED DESCRIPTION OF PREFERRED EMBODIMENTS

Figure 1:
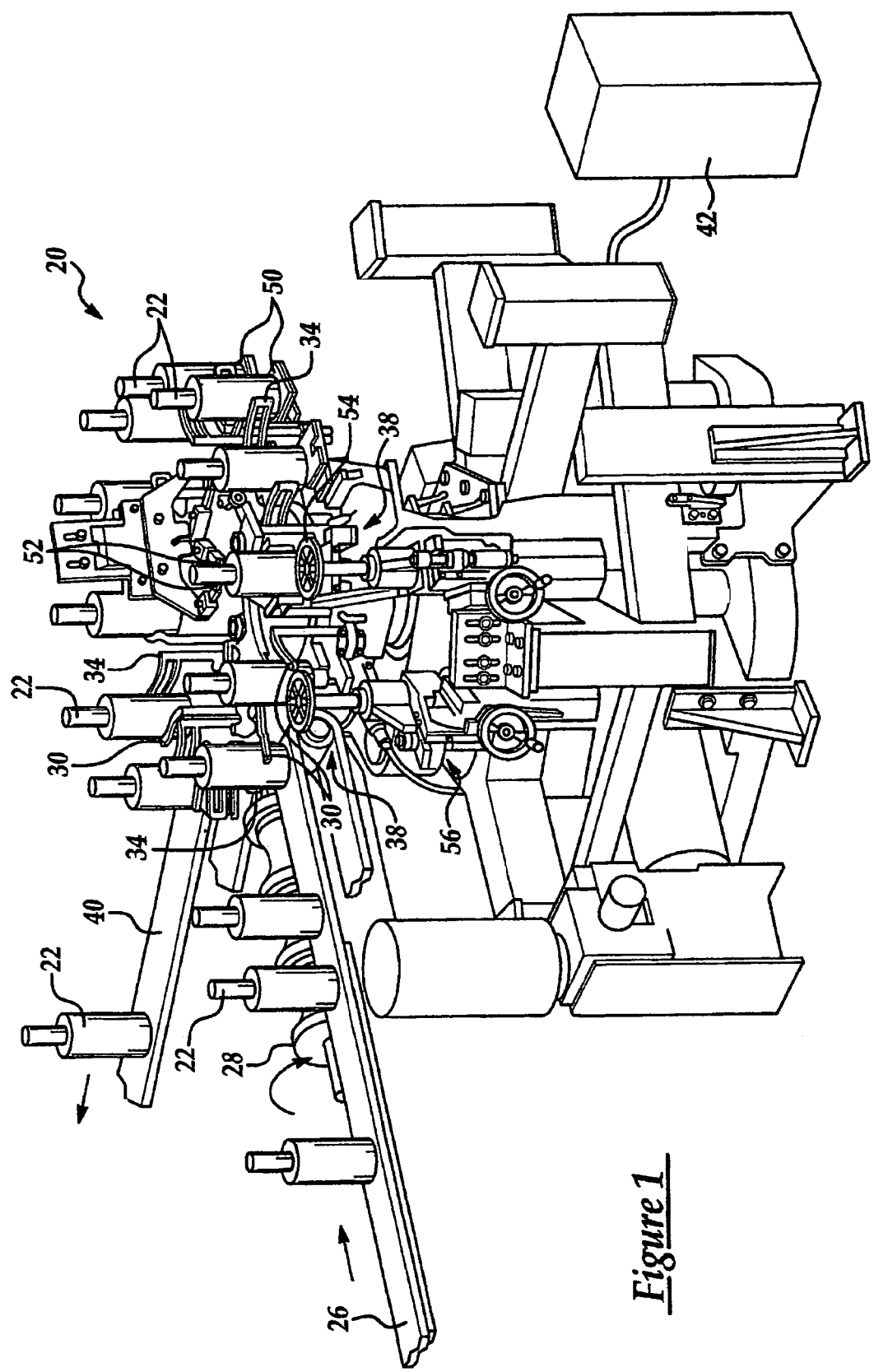
FIG. 1 shows an example of a glassware indexing apparatus with which the control system and method of the present invention may be used.
Figure 2:
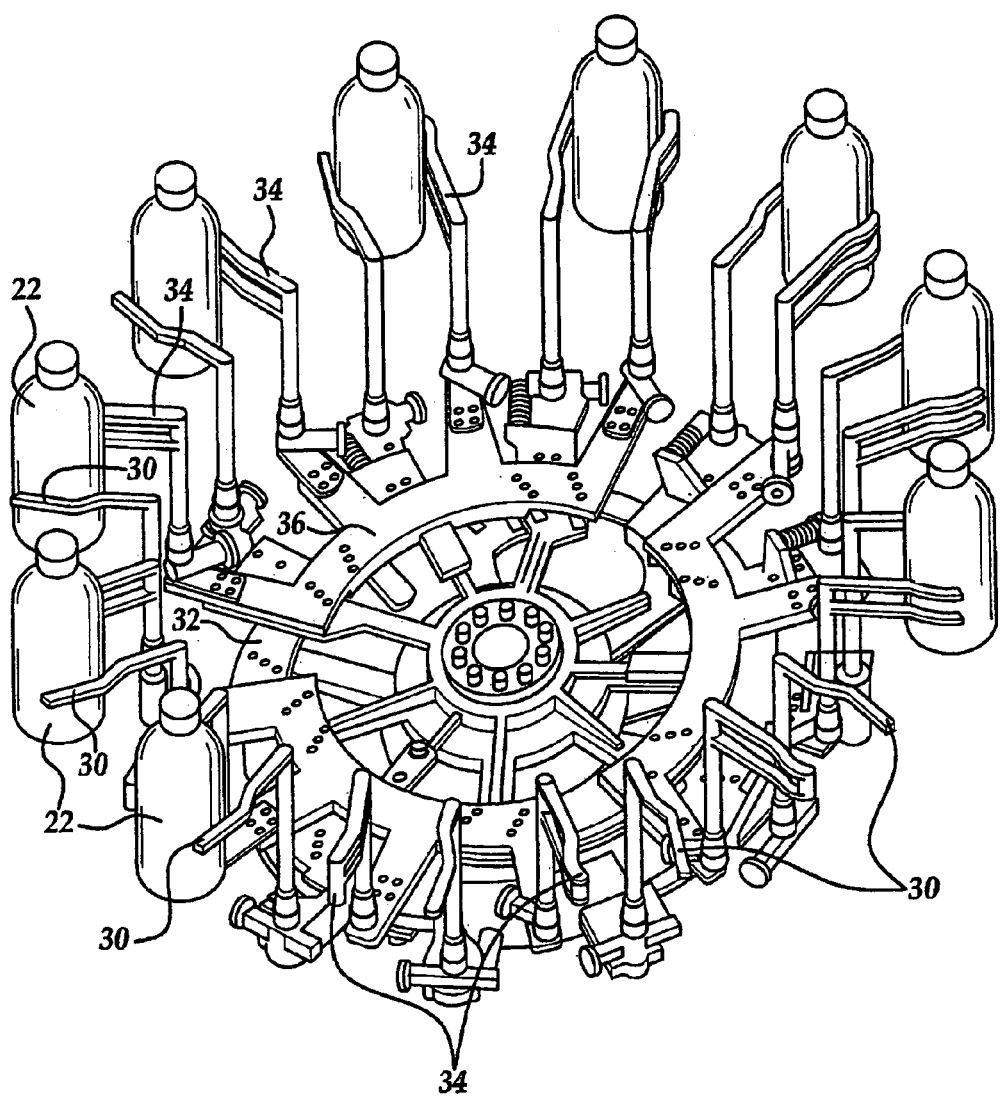
FIG. 2 is a perspective of the glassware indexing apparatus of FIG. 1, where only certain sections of the apparatus are shown.

FIGS. 1 and 2 illustrate an example of a glassware indexing and inspection apparatus 20 with which the control system and method of the present invention may be used. Apparatus 20 indexes glassware articles or containers between various inspection stations, hereafter referred to as 'inter-station' movement, as well as rotates, spins or otherwise moves the articles within at least one particular station, hereafter referred to as 'intra-station' movement. Of course, this is only one example of an apparatus that may employ the control system and method of the present invention, as numerous other apparatuses capable of using that control system and/or method also exist.

Mechanical Discussion

Indexing and inspection apparatus 20 transports articles of glassware 22, such as glass containers, through a series of inspection stations where various types of inspections may be performed. Apparatus 20 generally includes an infeed conveyer 26, an infeed device 28, a series of spring finger assemblies 30 connected to and supported by a lower carrier 32, a series of stationary finger assemblies 34 connected to and supported by an upper carrier 36, a series of inspection stations 38, an outfeed conveyer 40, and an electronic control system 42. Infeed conveyor 26, which can be an endless belt conveyor or other appropriate type of conveyor, brings containers in sequence and presents them to infeed device 28. The infeed device is driven by a servo motor 80 (FIG. 3) and assists in transitioning the lateral movement of infeed conveyor 20 to the rotational movement of finger assemblies 30, 34. Once the containers near the end of infeed conveyor 26, infeed device 28 positions them so that they are properly spaced and are ready to be received by finger assemblies 30, 34. The infeed device preferably acts as a sort of master timing reference for the overall apparatus 20, as the rotational position and/or rotational velocity of the infeed device can affect the timing and operation of many other components. For more detailed examples of infeed devices, including worm gear-type infeed devices, please see U.S. Pat. Nos. 6,386,353 issued to Gerber and 5,392,928 issued to Nickey et al., both of which are incorporated herein by reference.

The apparatus 20 preferably is of the type described in U.S. Pat. No. 6,581,751, the disclosure of which is also incorporated herein by reference. The inspection apparatus is not shown to facilitate illustration of the conveyor.

The lower and upper carriers 32, 36 (FIG. 2) are rotatably driven by separate servo motors 84, 82 (FIG. 3), thus allowing the carriers to co-rotate or to rotate with respect to one another. When one or both of the carriers rotate with respect to one another, finger assemblies 30, 34 are brought closer together such that they can grip a container 22 therebetween. Once the container is properly gripped, lower and upper carriers 32, 36 can co-rotate, thus causing inter-station movement of the container such that it is transported to an inspection station 38. It should be appreciated that the term 'carrier' is used in its broadest sense to encompass any type of device capable of indexing or otherwise transporting containers throughout an indexing and/or inspection apparatus, and is not necessarily limited to the preferred embodiment discussed herein. Furthermore, it is quite possible to have multiple servo motors operably coupled to a single carrier device. The arcuate path through which container 22 travels during inter-station movement is defined by what is referred to as a carry radius.

Figure 3:
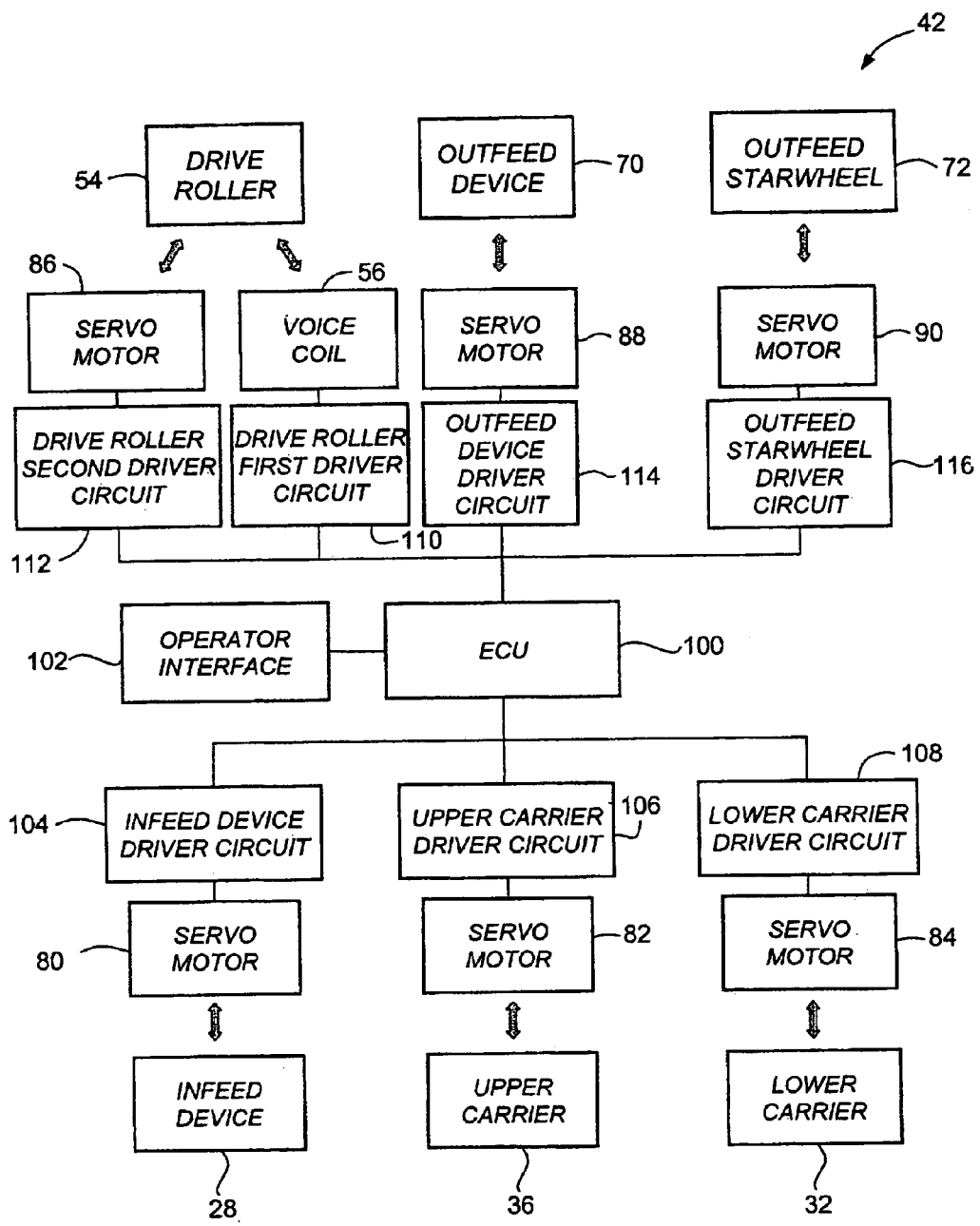
FIG. 3 is a block diagram of an embodiment of the control system of the present invention.

The inspection stations 38 preferably are spaced at equal angular increments around the circumference of apparatus 20, and each preferably includes a slide pad 50, at least one pair of free-wheeling back-up rollers 52, and a roller device or drive roller 54 that drives the intra-station movement of the container via a separate servo motor 86 (FIG. 3). In general, once container 22 is indexed into an inspection station 38, it is pushed radially inward from the carry radius to what is referred to as an "inspection radius." The inspection radius defines an imaginary arc that passes through each of the inspection stations 38 of apparatus 20; more specifically, the arc passes through the point in each inspection station where the container experiences intra-station movement about its own axis during inspection. Accordingly, the carry and inspection radii are concentric arcs, with the inspection radius being smaller and thus located at a position radially inward of the carry radius. It is worth noting that the inspection radius is a fixed radius that is not dependent on container diameter, which allows for fixed position inspection devices. Once the container enters the inspection station and is moved to the inspection radius, it preferably is placed on slide pad 50, which is a flat horizontal pad preferably having one or more rollers for allowing intra-station rotation of the container about its own axis. Free-wheeling back-up rollers 52 are located on the radially inward side of the container such that drive roller 54 can be moved in place and exert a force on the container without pushing it off of the slide pad. Radial movement of drive roller 54, which is responsible for the container moving between the carry and inspection radii, preferably is performed by a voice coil or actuator 56 (FIG. 3). The voice coil or actuator is basically a two-part solenoid-like actuator having electrical windings and a steel housing that support a magnetic core, and provides a force proportional to the amount of current supplied to its windings. This force output vs. current input arrangement makes the voice coil particularly well suited for provided variable force against the container; a variable force that is calculated by electronic control system 42 as a function of the container mass, inertia and acceleration rates, as will be subsequently explained in greater detail. Accordingly, voice coil 56 moves the container between the carry and inspection radii, but does not directly contribute to either inter-station or intra-station movement.

The finger assemblies release container 22. If the inspection requires container rotation, then drive roller 54 is brought into contact with the side of the container to impart rotational or intra-station movement. Drive roller 54 is rotationally driven by a separate servo motor 86 (FIG. 3), and rotates the container about its own axis for inspection or other purposes. Thus, voice coil 56 radially moves drive roller 54 into and out of contact with a container, while servo motor 86 rotationally drives drive roller 54 such that it causes intra-station movement of the container. The term "inspection" is used in its broadest sense to encompass any optical, electro-optical, mechanical or electrical observation or engagement with the container to measure or determine a potentially variable characteristic, including but not necessarily limited to mold codes and commercial variations. Two examples of inspection stations that could be utilized with apparatus 20 are shown in U.S. Pat. Nos. 6,256,095 issued to Ringlien and 6,175,107 issued to Junvinall, both of which are incorporated herein by reference. Once inspection is complete, drive roller 54 moves out of the way by deactivating voice coil 56, and the container is again moved to the carry radius where it begins further inter-station movement.

This sequence of events generally continues until each container 22 has cycled through all of the stations of apparatus 20, at which point the container is contacted by an outfeed device 70 (FIG. 3). In a preferred embodiment, the outfeed device is a set of pusher fingers (not shown) that transport the container to an outfeed conveyor 40. The outfeed device is driven by a servo motor 88 that is electronically geared to infeed device 28 such that movement of the infeed device causes a synchronized or proportional movement of the outfeed device, but not necessarily at precisely the same rate. The containers are transported to an outfeed starwheel 72 (FIG. 3) which is driven by a servo motor 90 that is electronically geared to infeed device 28. The outfeed starwheel is geared such that the container throughput of the infeed device and the outfeed starwheel are the same. Following transportation through the outfeed starwheel onto outfeed conveyor 40, the container either enters a cullet or reject chute for removing containers that did not pass inspection, or is transported to a subsequent stage in the manufacturing or packaging process for those containers that did pass inspection. More detailed examples of an outfeed starwheel and of a glassware indexing apparatus in general can be respectively found in U.S. Pat. Nos. 5,613,593 issued to Gerber and 6,581,751 B1 issued to Nickey et al. Both of these patents are herein incorporated by reference.

Electrical Discussion

Turning now to FIG. 3, there is shown a general overview of the electronic control system 42 of the present invention. Control system 42 oversees both inter-station and intra-station movement of containers 22 throughout apparatus 20 and is capable of, among other features, driving servo motors 80-90 at optimum speeds based on the physical parameters of the container being transported. Control system 42 generally includes an electronic control unit (ECU) 100, an operator interface 102, an infeed device driver circuit 104, an upper carrier driver circuit 106, a lower carrier driver circuit 108, a drive roller first driver circuit 110, a drive roller second driver circuit 112, an outfeed device driver circuit 114, an outfeed starwheel driver circuit 116, and various communication buses for interconnecting the electronic components. ECU 100 can be provided according to one of numerous embodiments, examples of which include but are not limited to a dedicated computer, an application specific integrated circuit (ASIC), and one or more microprocessors and/or microcontrollers, to name but a few. In a preferred embodiment, ECU 100 broadly comprises a combination of the above listed items to provide coordinated, closed-loop control of driver circuits 104-116. In an even more preferred embodiment, the ECU comprises a microprocessor for running the global application which is coordinated with, via shared memory, multiple digital signal processing (DSP) boards. The DSP boards coordinate inter-station movement, intra-station movement, trajectories and closed-loop position and velocity loops, and are coupled via a firewire bus to individual driver circuits using dedicated DSP chips to perform closed-loop control of the current loops. Although driver circuits 104-116 are shown in FIG. 3 as separate stand alone circuits, it is possible to have them integrated into one or more larger circuits.

Operator interface 102 can also assume one of many different forms, but preferably includes a graphical user interface (GUI) loaded on a stand along computer or some other device having input/output capabilities. The interface preferably integrates all of the operator-input controls for apparatus 20, including those pertaining to inter-station and intra-station movement. The operator interface should also provide diagnostic information so that an operator can identify jams, shut-downs, or other problems occurring within apparatus 20.

Each of the driver circuits 104-116 is electronically coupled to a corresponding servo motor, and preferably includes an electronic memory device, an electronic processing device, an angular position sensor, and a signal input and output. The electronic memory device of each of the driver circuits can store a "motion profile," which is a sequence of commands similar to an executable file. Reception of a trigger signal, which also is referred to as a programmable limit switch (PLS) signal, causes the driver circuit's electronic processing device to execute the motion profile stored in the memory. A motion profile includes instructions that can cause a driver circuit to do a variety of tasks, including controlling the operation of a servo motor, generating a separate trigger signal which in turn activates another motion profile, or causing the angular position sensor to monitor the corresponding servo motor, to name but a few. Once the commands of a motion profile are executed, the driver circuit returns the servo motor to a predetermined position and waits for the next trigger signal. Of course, execution of a motion profile could be triggered through inter-circuit or intra-circuit logic, instead of via the trigger signal approach discussed above.

Software Discussion—Controlling Movement of Containers

Figure 4:
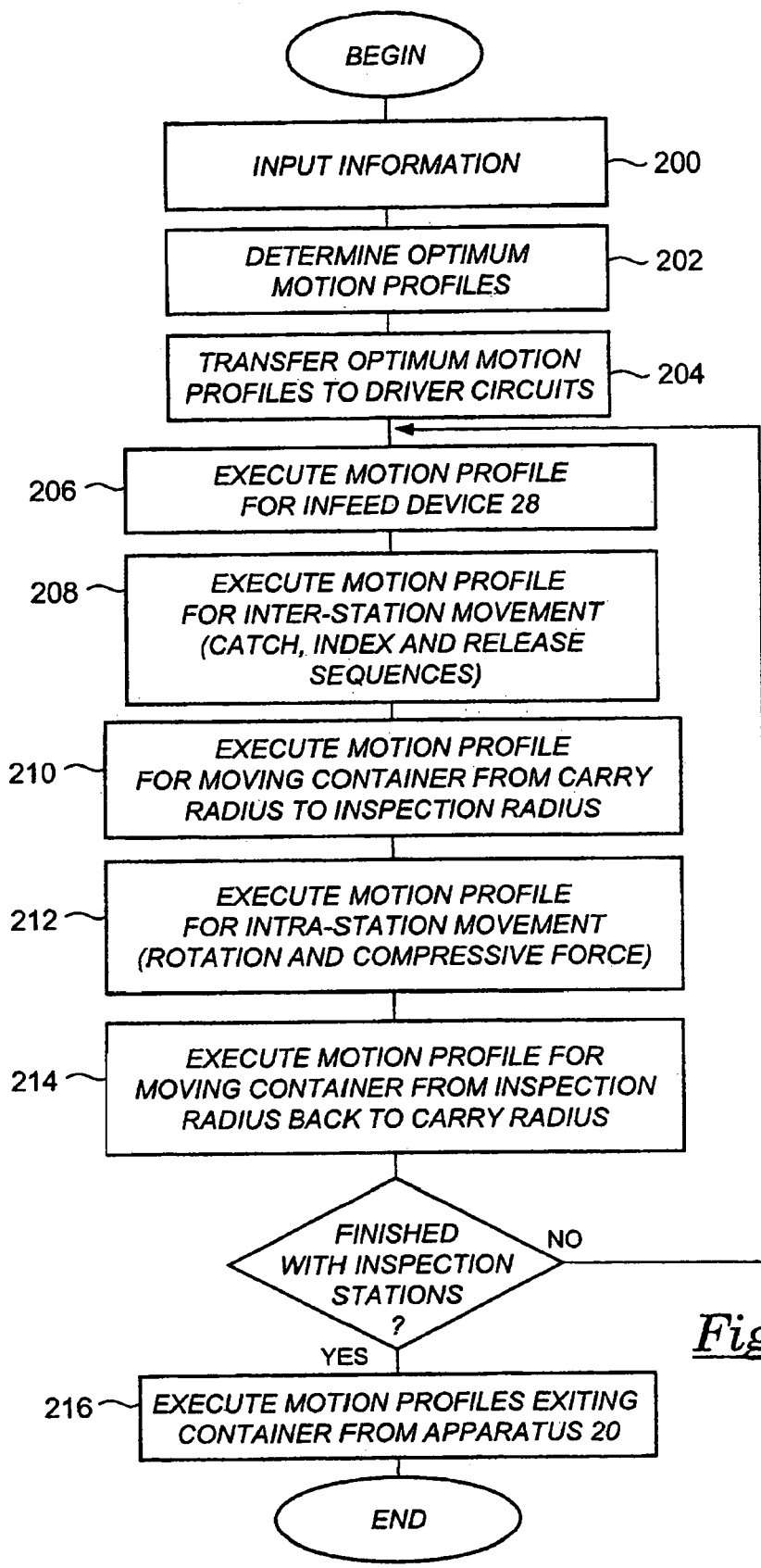
FIG. 4 is a flowchart of a method for operating the control system of FIG. 3.

The flowchart shown in FIG. 4 is a general overview of a preferred method for controlling the movement of containers through indexing and inspection apparatus 20. Step 202 is specifically directed to a method for determining an optimum motion profile for each of the servo motors 80-90, and is further explained in connection with the more detailed flowchart of FIG. 5 and the timing charts of FIGS. 6-8.

Beginning with step 200, an operator enters various items of information into electronic control system 42 through operator interface 102. These items of information can include structural and/or technical data about one or more components of indexing and inspection apparatus 20. Examples of structural and/or technical data on the apparatus or its components can include: infeed device information, finger assembly information, and upper and lower carrier information. Infeed device information preferably includes data on the pitch of infeed device 28 and on the distance between the infeed device and lower and upper carriers 32, 36. Finger assembly information preferably includes data points or other structural data that describe the mechanical shape and other characteristics of the finger assemblies, both spring and fixed finger assemblies 30, 34. Carrier information preferably includes data on lower and upper carriers 32, 36, including the carry radius. Of course, these are only some of the items of information that can be entered, as other data may also be needed. Once the appropriate information has been entered and any other required setup steps have been completed, operation passes to step 202.

Step 202 involves determining an optimum motion profile for each of the servo motors 80-90. More specifically, ECU 100 executes an application which calculates optimum motion profiles for each servo motor based upon the physical characteristics (size, shape, weight, etc.) of the containers being transported, as well as known constraints of indexing and inspection apparatus 20. Each optimum motion profile is tailored to control a certain servo motor such that the servo motor delivers optimum inter-station, intra-station, or another type of movement, depending on its job. One goal of an optimum motion profile is to efficiently distribute cycle time and thermal energy between the various servo motors 80-90 of apparatus 20, thereby increasing the overall throughput of the apparatus while decreasing thermal stress on any one servo motor. A more detailed description of step 202 is subsequently provided in conjunction with the flowchart of FIG. 5 and timing charts of FIGS. 6-8.

Once a set of optimum motion profiles has been developed, they are transferred to their respective driver circuits 104-116, step 204. Each motion profile is received over a signal input of the appropriate driver circuit, and is stored in the driver circuits' electronic memory device. There it remains inactive until reception of a trigger signal, which causes the electronic processing device of that driver circuit to execute the motion profile. This results in a coordinated operation of all the individual driver circuits. Turning now to steps 206-216, the execution of several motion profiles is described. It should be noted that the sequence of execution of motion profiles could occur in a different order than that described here. Also, additional motion profiles could be executed, or some of the motion profiles shown here could be omitted, to name but a few alternative scenarios.

In step 206, infeed device driver circuit 104 executes a motion profile which causes the overall operation of apparatus 20 to be synchronized with the rotational position and speed of infeed device 28. The motion profile causes the angular position sensor of circuit 104 to track the rotational position of servo motor 80, and send a trigger signal when that servo motor reaches a predetermined angular position. Servo motor 80 preferably makes one full rotation per container that passes through the infeed device; a full rotation is divided into a certain number of angular increments such as 1,000. Thus, the angular position sensor tracks the rotational position of servo motor 80 and reports its angular position as a number from 1 to 1,000. The motion profile stored in circuit 104 instructs the circuit to output one or more trigger signals when the angular position sensor reports that servo motor 80 is at a certain angular position. These trigger signals can initiate execution of one or more other motion profiles stored on different driver circuits, thereby synchronizing the movement of other servo motors to that of servo motor 80. For example, when the servo motor is at incremental angular position 386, the motion profile causes circuit 104 to send a trigger signal to circuit 106 to begin rotating upper carrier 36 into position. The motion profile may also instruct circuit 104 to send a second trigger signal to circuit 108 when the incremental angular position of servo motor 80 is 400, thus causing rotation of lower carrier 32. Parameters used to calculate the actual incremental angular position that initiates a trigger signal may include: the amount of time required for container 22 to travel from the end of infeed device 28 to finger assemblies 30, 34, the anticipated position of the container once it is grasped by the finger assemblies, as well as portions of the infeed device information, finger assembly information, and upper and lower carrier information, as entered in step 200.

In step 208, motion profiles stored on driver circuits 106 and 108 are executed and cause inter-station movement of container 22. Inter-station movement of the container, either between the infeed device and a first inspection station or between inspection stations, generally includes a catch sequence where the finger assemblies grasp the container, an indexing sequence where the container is transported along the carry radius, and a release sequence where the finger assemblies release the container. During inter-station movement, driver circuits 106, 108 execute optimum motion profiles which respectively cause servo motors 82, 84 to rotatably drive upper and lower carriers 36, 32.

In the catch sequence, upper carrier 36 begins to rotate first such that fixed finger assembly 34 contacts the container and begins to sweep it out of the loading position slightly before spring finger assembly 30 begins rotating. The catch sequence preferably is initiated by a trigger signal sent first to upper carrier driver circuit 106 (incremental position 386) followed by a subsequent trigger signal sent to lower carrier driver circuit 108 (at incremental position 400). Once the fixed finger assembly and container are moving together, lower carrier 32 begins rotating spring finger assembly 30 in the same direction. This movement of the spring finger assembly just before being contacted by the container acts as a sort of head-start to prevent the moving container from abruptly contacting a stationary spring finger assembly. At first, the two finger assemblies 34, 36 are rotating at slightly different rotational velocities, with the fixed finger assembly and container rotating slightly faster than the spring finger assembly. This difference is absorbed by the spring nature of the spring finger assembly, such that the container is gently captured in compression between the two finger assemblies. The catch sequence is preferably followed by the indexing sequence.

During the indexing sequence, servo motors 82, 84 respectively drive upper and lower carriers 36, 32 such that both finger assemblies rotate at the same acceleration and deceleration. The rotational velocity of the upper and lower carriers is accelerated until servo motors 82, 84 reach a certain angular position, as sensed by angular position sensors in circuits 106, 108. Once this angular position is detected, the servo motors decelerate the rotational velocity of the carriers until the finger assemblies are stationary. It should be understood that one or more periods of constant rotational velocity may be inserted between the acceleration and deceleration periods. During the acceleration period, compression on container 22 by the finger assemblies is increasing; while during the deceleration period, finger assembly compression is decreasing. The compression during inter-station movement should always remain above a certain point so that the container is not dropped by the finger assemblies.

In the release sequence, driver circuit 106 causes the spring finger assembly to release the container such that it may be engaged by drive roller 54 and pushed into an awaiting inspection station 38. To release container 22, a motion profile instructs circuit 106 to forwardly accelerate the upper carrier such that the leading spring finger assembly 30 pulls away from the container. This causes the spring finger assembly to unwind thereby decreasing the compressive force exerted on the container, and ultimately freeing the container for radial movement by the driver roller. Once the spring finger assembly is away, a motion profile executed by drive roller first driver circuit 110 instructs voice coil 56 to move drive roller 54 into place and contact the container such that it is rolled down the fixed finger assembly. The specific values pertinent to inter-station movement, such as acceleration and deceleration rates, angular positions, etc., are preferably tailored to the specific apparatus 20 and container 22 at hand.

Step 210 involves pushing container 22 radially inward from the carry radius to the inspection radius. Execution of a motion profile by drive roller first driver circuit 110 causes voice coil 56 to output a mechanical force that moves drive roller 54 into place. Execution of this motion profile preferably occurs when the upper and lower carriers are still some distance away from the inspection station (still in inter-station movement). For instance, when upper and lower carriers 36, 32 are 4° away from inspection station 38, a trigger signal preferably is sent by circuit 108 to circuit 110, which initiates execution of the motion profile. Accordingly, movement of the carriers is synchronized to that of the drive roller. The moment container 22 comes to an inter-station stop, drive roller 54 is already moving and almost immediately thereafter pushes the container radially inward towards the inspection radius.

In order to facilitate a smooth transition from the outer carry radius to the inner inspection radius, fixed finger assembly 34 is oriented such that it guides container 22 as the drive roller rolls the container along the fixed finger assembly and places it on slide pad 50. Once the container is contacted by the drive roller and is moving towards the inspection radius, the motion profile stored on circuit 108 instructs the lower carrier to accelerate the fixed finger assembly in reverse away from the container. Stated differently, fixed finger assembly 34 moves in the opposite rotational direction as it had been moving, to an out-of-the-way position. This reverse motion ensures that the fixed finger assembly will not interfere with the entry of container 22 into inspection station 38.

In step 212, the container simultaneously experiences intra-station movement and is captured in pressed between drive roller 54 and free-wheeling back-up rollers 52, during which time it may be inspected according to one of many techniques known in the art. The term "inspection" is used in its broadest sense to encompass any optical, electro-optical, mechanical or electrical observation or engagement with the container to measure or determine a potentially variable characteristic, including but not necessarily limited to mold codes and commercial variations. Some inspections require no intra-station movement, in which case, the inspection would simply proceed without the container being rotated about its axis. The intra-station movement experienced in step 212 is a result of a motion profile executed by second driver circuit 112, while the compressive force is a result of a motion profile executed by first driver circuit 110. Circuit 112 instructs servo motor 86 to rotate container 22 about its axis, such that it first undergoes an acceleration sequence where the rotational velocity is increasing, followed by an inspection sequence, and ending with a deceleration sequence where the rotational velocity is decreasing. The total time allotted for the acceleration, inspection and deceleration sequences must be sufficient for inspection of whatever feature is being inspected. Furthermore, the inspection sequence should be carried out at a rotational speed sufficient for inspection, as different types of inspections may require different minimum or maximum rotational speeds.

As mentioned, drive roller 54 exerts a compressive force on the container during intra-station movement such that the container is rotatably trapped between driver roller 54 and the one or more pairs of free-wheeling back-up rollers 52. This prevents the container from inadvertently slipping out of inspection station 38 while it is being rotated. The amount of compressive force required varies during intra-station movement, depending on which operational sequence the system is in. For example, during the acceleration and deceleration sequences, voice coil 56 exerts an increased amount of compressive force against the container. During the inspection sequence, which generally experiences a constant rotational velocity, the amount of compressive force is reduced. This helps to reduce wear on the roller bearings, as well as the duty cycle and operating temperature of voice coil 56. Other factors, such as the physical characteristics of the container, can influence the amount of compressive force needed. For instance, the amount of force required properly to maintain a heavy container during rotation is different than that required to maintain a light container during the same rotation. Once inspection is complete and a new cycle of inter-station movement is ready to begin, circuit 110 causes voice coil 56 to retract drive roller 54 and move away from the still rotating container.

Step 214 involves reentry of container 22 into the carry radius from the inspection radius. Immediately following step 212, container 22 is still rotating around its axis. Upper carrier 36 moves fixed finger assembly 34 such that it contacts the rotating container and uses its rotation to roll the container up the fixed finger assembly. As previously explained in step 208, the fixed finger assembly contacts the container first, such that the two begin moving towards the awaiting spring finger assembly. Slightly before the container is about to contact spring finger assembly 30, the lower carrier begins rotating in the same direction such that contact is made once the spring finger assembly has a non-zero rotational velocity. This sequence of inter-station and intra-station steps continues until container 22 has indexed through all of the inspection stations of apparatus 20 and is ready to exit the machine.

Step 216 involves the transfer of container 22 from the grasp of the finger assemblies 30, 34 to outfeed device 70, and ultimately the exiting of the container from apparatus 20. The outfeed device 70 is electronically geared to infeed device 28, such that movement of the outfeed device is proportional to that of the infeed device; however, they do not need to be the same. Execution of a motion profile by outfeed device driver circuit 114 causes the outfeed device to begin moving as finger assemblies 30, 34 begin releasing the container. The outfeed device accelerates from its resting position to the point at which it contacts container 22, and continues accelerating with the container until the point where the container is presented to outfeed starwheel 72. This constant and continuous acceleration helps with the vertical alignment of the container, as any tilt of the container is corrected before the container hits the starwheel. Even if the container is falling when the outfeed device first contacts it, the acceleration rate of the outfeed device is greater than that of gravity, thus the container straightens up prior to reaching outfeed starwheel 72.

Outfeed starwheel 72 is also electronically geared to infeed device 28 such that these two components operate at the same container throughput rate. The rotational velocity of starwheel 72 depends on the number of pockets contained in the starwheel, which is a function of the container diameter. Thus, if infeed device 28 slows down to a certain container throughput speed, so too will the starwheel. This guarantees that the overall rate of containers entering apparatus 20 is the same as the overall rate exiting the apparatus. The electronic gearing taking place between the infeed device and the outfeed device, as well as the infeed device and the outfeed starwheel, is provided by circuits 104 and 114, and circuits 104 and 116, respectively. These components can be electronically geared to one another according to methods known in the art.

Software Discussion—Determining Optimum Motion Profiles

Figure 5:
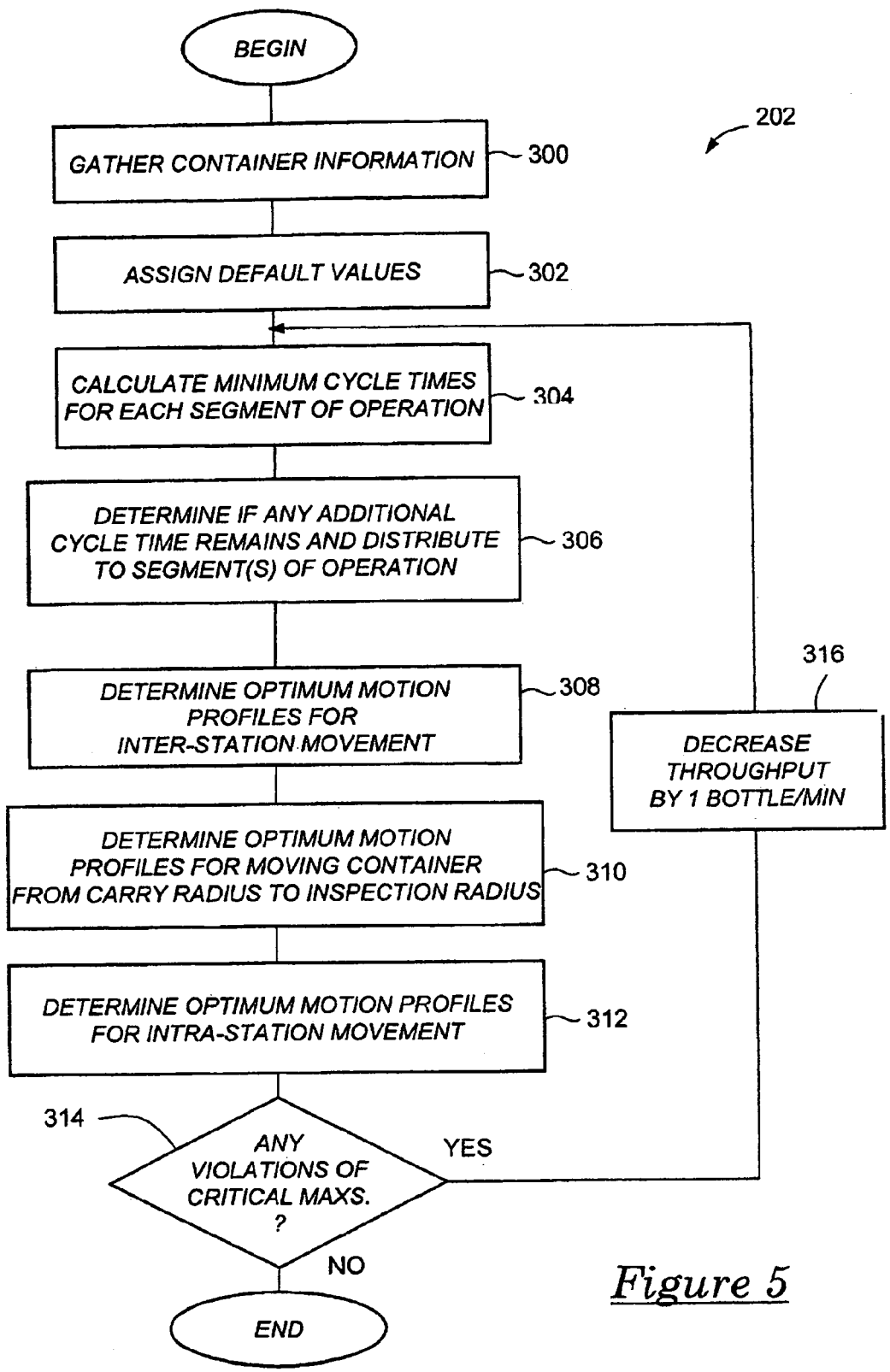
FIG. 5 is a flowchart that breaks out and details step 202 of FIG. 4.

Turning now to FIG. 5, step 202 is broken out into a sequence of more detailed sub-steps. The flowchart of FIG. 5 and the timing charts of FIGS. 6-8, describe a preferred method for determining optimum motion profiles for servo motors 80-90. It is a goal of these optimum motion profiles to drive each servo motor at a maximum speed, yet still take into consideration known constraints of apparatus 20, which are referred to as critical maximums. The term 'critical maximum' is broadly used to include any known constraint or limitation of indexing and inspection apparatus 20, or those of any of the apparatus' components.

For example, if the containers being transported through apparatus 20 are heavy, then rapid deceleration by the upper and lower carriers 36, 32 during inter-station movement can exert too great a force against spring finger assembly 30, which may have a detent force limit of roughly 13 pounds for example. Thus, the deceleration of the upper and lower carriers may need to be reduced in order to satisfy this critical maximum of the spring finger assembly. As another example, containers are more likely to be thrown out of inspection station 38 during intra-station movement when high rates of acceleration are involved. To prevent this, one of several things can be done. One solution is to increase the amount of force exerted by drive roller 54 by increasing the force from voice coil 56; this causes the drive roller to press more tightly against the container. But the duty cycle of the voice coil may be a limiting critical maximum. Another possible solution is to allocate more time to the intra-station acceleration sequence, thus reducing the amount of compression required by the drive roller. While this approach addresses the voice coil duty cycle critical maximum, it also increases the amount of cycle time for this particular inspection step. These types of considerations and tradeoffs are made by the recursive search algorithm executed by ECU 100. Other examples of critical maximums include, but certainly are not limited to, the maximum rotational velocity for intra-station movement where accurate inspection can still be performed, the maximum duty cycle of each servo motor, and the maximum amount of force that can be applied against the finger assemblies.

In general, electronic control system 42 executes a recursive algorithm that utilizes information about the containers being transported, as well as critical maximums of the indexing and inspection apparatus, to determine one or more optimum motion profiles for use with one or more servo motors. The term "recursive algorithm" is used in its broadest sense to include any type of step-by-step procedure for accomplishing a defined goal, where the procedure is generally repetitive depending upon the state of one or more conditions. Execution of this algorithm typically results in the failure or violation of one or more of the critical maximums. In response to these anticipated violations, the algorithm redistributes, shifts, adds, subtracts, or otherwise alters one or more parameters of the motion profile being developed, and then retests the new motion profile. The reiterative algorithm continues to adjust operating parameters, such as the amount of cycle time used by each segment of servo motor operation, until a single critical maximum emerges as the primary bottleneck. The algorithm then focuses on this single critical maximum and applies whatever additional cycle time is available to the area of concern. Providing additional cycle time for a particular segment of servo motor operation allows the servo motor to run slower during that segment, thus possibly complying with a critical maximum that would otherwise be violated. Once a motion profile is developed that satisfies this first critical maximum, the reiterative algorithm moves onto the next emerging critical maximum and amends the motion profile such that it satisfies both critical maximums, and so on. This iterative process of adjustment and retesting continues until all of the predefined critical maximums of apparatus 20 are obeyed; at which point, an optimum motion profile has been developed. One by one, the ECU creates optimum motion profiles for each of the servo motors 80-90.

Beginning with step 300, information is entered on the particular container being transported through apparatus 20. Examples of container information gathered include, but are not limited to, the following:

TABLE 1

| Container Parameter | Symbol |
|---|---|
| Diameter of Container, at Point of Inspection | BOTTLE INSPEC DIA |
| Diameter of Container, at Point of Contact with Drive Roller | BOTTLE CONTACT DIA |
| Mass of Container | BOTTLE MASS |

It should be pointed out that the particular order that information is entered, whether it be container information or information pertaining to apparatus 20, could vary from the exemplary embodiment discussed here. As an example, the container information could have been entered back in step 200, instead of being entered currently.

In step 302, ECU 100 first assigns default values to a series of operating parameters. These operating parameters can include, for example, the following:

TABLE 2

| Profile Parameter | Symbol |
|---|---|
| Minimum Cycle Time - Inter-station Movement | $\tau_{INTER\text{-}STATION}$ |
| Minimum Cycle Time - Carry-to Inspection-Radius Movement | $\tau_{CARRY\text{-}INSPEC}$ |
| Minimum Cycle Time - Intra-station Movement (Standard Inspection) | $\tau_{INTRA\text{-}STATION(STD)}$ |
| Minimum Cycle Time - Intra-station Movement (Mold Code Inspection) | $\tau_{INTRA\text{-}STATION(CID)}$ |
| Minimum Cycle Time - Inspection-to Carry-Radius Movement | $\tau_{INSPEC\text{-}CARRY}$ |
| Minimum Rotational Velocity Needed for Standard Inspection | $\omega_{INSPEC\_START}$ |
| Minimum Rotational Velocity Needed for Mold Code Inspection | $\omega_{CID\_INSPEC\_START}$ |
| Minimum Acceleration Time Needed for Standard Inspection | $\tau_{INSPEC\_ACL}$ |
| Minimum Acceleration Time Needed for Mold Code Inspection | $\tau_{CID\_INSPEC\_ACL}$ |
| Maximum Rotational Speed for Standard Inspection | $\omega_{INSPEC}$ |
| Maximum Rotational Speed for Mold Code Inspection | $\omega_{CID\_INSPEC}$ |
| Minimum Number of Revolutions Needed for Standard Inspection | STANDARD_RATIO |
| Minimum Number of Revolutions Needed for Mold Code Inspection | CID_RATIO |
| Radius of Standard Inspection | RADIUS_INSPECTION |
| Radius of Mold Code Inspection | RADIUS_CID_INSPECTION |

Of course, these default values are dependent upon may factors, including the particular type of apparatus 20 being used, as well as the physical characteristics of container 22. At this point, an overall container throughput speed (THROUGHPUT) for apparatus 20 is also assigned. For instance, a desired throughput speed of 300 bottles/min would result in an overall cycle time ($\tau_{CYCLE\_DEFAULT}$) of 200 msec/bottle.

Turning now to step 304, the algorithm first determines the amount of cycle time needed for each segment of operation based on the container information and default parameters previously entered; the calculated cycle times are referred to as "minimum cycle times." Once the control system has determined minimum cycle times for each segment of operation, the system subtracts each of those minimum cycle times from the overall cycle time (200 msec/bottle for a throughput of 300 bottles/min), and determines if there is any remaining time. If there is remaining time, then it is distributed between the segments that need it most, as will be explained. With brief reference to FIG. 4, minimum cycle times must be calculated for inter-station movement step 208, for moving the container from the carry radius to the inspection radius step 210, and for intra-station movement step 212. Assume the default value for the minimum cycle time for inter-station movement is 84 msec ($\tau_{INTER\text{-}STATION}$), and the default value for the minimum cycle time for moving the container from the carry-radius to the inspection-radius is 19 msec ($\tau_{CARRY\text{-}INSPEC}$). A minimum cycle time must still be generated for the intra-station movement segment. In order to derive a minimum cycle time for the intra-station movement, the algorithm must determine if standard inspection of a container (inspection for commercial variations) or mold-code inspection takes longer; whichever takes longer is the bottleneck, and is thus the value used to determine the overall minimum cycle time of the operation.

Figure 8:
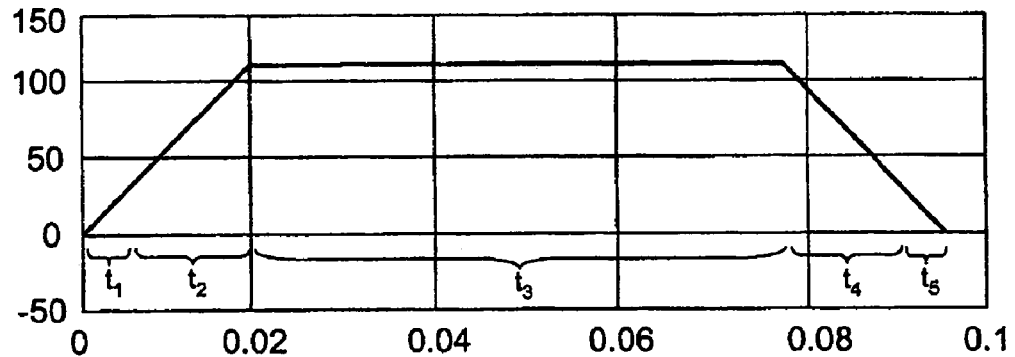
FIG. 8 is a timing chart for an optimum motion profile corresponding to step 212 of FIG. 4.

With reference to the timing chart of FIG. 8, the total amount of time needed for standard inspection ($\tau_{INTRA-STATION(STD)}$)=$t_1+t_2+t_3+t_4+t_5$. Time interval $t_1$ is a period of rotational acceleration before inspection begins, and preferably extends from the beginning of rotation until the container has reached 10% of its overall inspection acceleration. Time interval $t_2$ is a period of rotational acceleration during which inspection is being conducted. Time interval $t_3$ is a period of constant rotational velocity during which the container is being inspection. Time interval $t_4$ is a period of rotational deceleration during which the container is inspected (counterpart to $t_2$). Lastly, time interval '$t_4$ pertains to a period of rotational deceleration after inspection has ceased (counterpart to $t_1$), and preferably covers the period of time from when the container has reached 90% of its rotational deceleration until it stops rotating. For exemplary purposes, assume this calculation returned a standard inspection time of 96 msec, and a similar calculation for mold code inspection returned a time of 95 msec. In such a case, the standard inspection takes longer than the mold code inspection, and is thus the minimum cycle time for intra-station movement that is used during step 304. The time needed for moving container 22 from the inspection radius back to the carry radius is, in this example, included within the intra-station minimum cycle time calculation performed above and thus need not be separately considered. Examples of parameters that the algorithm could use for performing the calculations of step 304 include: $\omega_{INSPEC\_START}$, $\tau_{INSPEC\_ACL}$, $\omega_{INSPEC}$, $STANDARD\_RATO$, and $RADIUS\_INSPECTION$.

Figure 6:
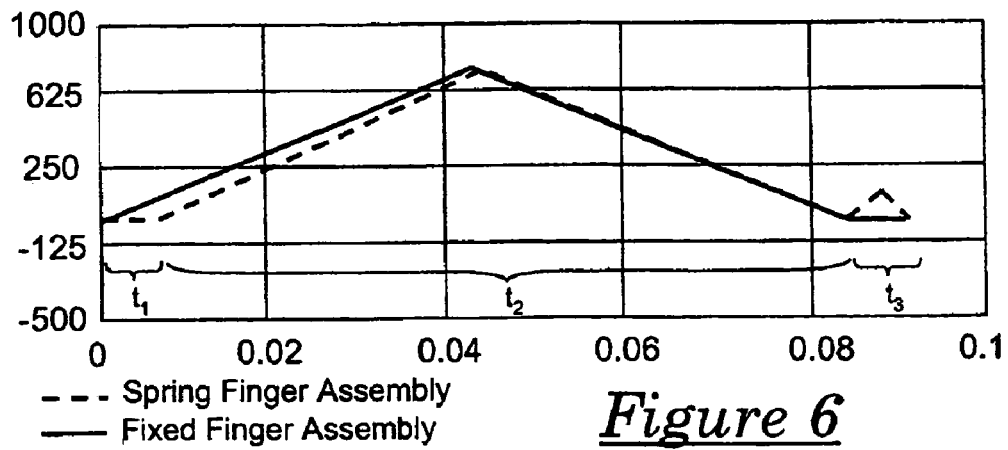
FIG. 6 is a timing chart for an optimum motion profile corresponding to step 208 of FIG. 4.

Step 306 subtracts the minimum cycle times calculated above from the overall cycle time, and distributes any remaining time to one or more segments of operation. More specifically, the minimum cycle times for $\tau_{INTER-STATION}$, $\tau_{CARRY-INSPEC}$, and the longer of $\tau_{INTRA-STATION(STD)}$ and $\tau_{INTRA-STATION(CID)}$ are subtracted from the overall cycle time (200 ms−84 msec−19 msec−96 msec=1 msec). Thus, at a throughput rate of 300 bottles/min and using the default values provided, an additional 1 msec/bottle of cycle time remains. Preferably, any additional time will be equally divided among the inter-station and intra-station segments (inter-station segment now receives 84.5 msec/bottle, and intra-station segment now gets 96.5 msec/bottle). Of course, the additional time can be distributed according to other distributions;

Now that minimum cycle times have been assigned to each segment of operation, more detailed motion profiles can be built for servo motors 80-90 that conform to those minimum cycle times. In step 308, the algorithm constructs an optimum motion profile for the inter-station segment of operation (step 208), which generally comprises the catch sequence, the index sequence, and the release sequence. An example of a typical timing chart is shown in FIG. 6 and plots the velocity of both the spring and fixed finger assemblies 30, 34 versus time, as carried by lower and upper carriers 32, 36, respectively. The catch sequence is approximated by $t_1$, which as seen in the chart and previously explained in connection with step 208, includes a constant acceleration by fixed finger assembly 34, and a delayed start followed by a constant acceleration by spring finger assembly 30. Because the upper and lower carriers are driven by servo motors 82, 84, respectively, critical maximums of those servo motors affect the acceleration rate shown in the chart.

The index sequence is generally represented in FIG. 6 by time period $t_2$. In addition to acceleration-related concerns, calculation of a motion profile for the index sequence must take into account the amount of compression exerted upon container 22. A certain amount of compression must be exerted by the finger assemblies upon the container such that the container does not fall during inter-station movement. Preferably, the algorithm has a desired compression (such as ⅛ inch), and knows the carry radius and the mechanical specifics of the finger assemblies (finger assembly information entered in step 200), such that optimum motion profiles for both the fixed and spring finger assemblies can be developed. Not until about halfway through the index sequence, are the finger assemblies moving at the same velocity. Different velocities by the two finger assemblies creates relative movement between them, thus resulting in either compression or decompression on the container. A goal when developing this timing chart is to minimize the acceleration rates experienced during inter-station movement, while still satisfying the minimum cycle time restraints (84.5 ms). It is known how many degrees each of the carriers must travel in a certain amount of time, thus, the algorithm is able to derive a velocity vs. time chart, similar to that of FIG. 6. The integral of each of the velocity curves is the distance covered during inter-station movement by that finger assembly, and the derivative of that curve is the acceleration. The recursive algorithm aims to develop an optimum motion profile for the index sequence that satisfies several objectives, including: moving the carriers through a certain angular distance in the least amount of time, yet doing so at the lowest acceleration, and satisfying all applicable critical maximums.

The release sequence is represented as $t_3$, and preferably follows a relaxation of the finger assembly compression on container 22. By relaxing the compression before releasing the container, the amount of container wobble due to stored energy in the spring finger assembly is minimized. As previously explained in connection with step 208, the release sequence for lower carrier 32 involves advancing spring finger 30 away from the container once the container is being pushed into the inspection station. Examples of parameters that the algorithm uses when performing the catch, indexing and release sequence calculations of step 308 include: finger assembly information, $_{BOTTLE\_MASS}$, $\tau_{INTRA-STATION}$, the distance from the carrying radius to the inspection radius, and the diameter of the bottle.

Step 310 determines optimum motion profiles for moving a container from the carry radius to the inspection radius (step 210). More specifically, the algorithm derives an optimum motion profile for drive roller first driver circuit 110, so that circuit 110 can provide voice coil 56 with an optimum amount of electrical current. Turning now to the timing chart shown in FIG. 7, a motion profile is derived for voice coil 56 that includes segments $t_1$-$t_6$. This motion profile dictates the amount of force drive roller 54 exerts against the container when moving it from the carry to the inspection radius, and can be broken up into several segments.

In a first segment $t_1$, a negative force is applied to the arm carrying drive roller 54 such that it causes the drive roller to be outwardly retracted to an out-of-the-way position, thus allowing carrier discs 32, 36 to deliver container 22 to this inspection station without getting fouled up on the drive roller. During a second segment of operation $t_2$, a constant negative force is applied to the drive roller such that it is maintained in the out-of-the-way position for a certain period of time. In order to determine the particulars for segments $t_1$ and $t_2$, step 310 preferably calculates the following: the amount of time needed for each segment, the inertia created during each segment, the reverse distance traveled by the drive roller, the acceleration rate of the reverse movement, and the amount of force with which voice coil 56 maintains drive roller 54 in an out-of-the-way position.

A third segment $t_3$ is initiated when it is time to move drive roller 54 into position and push container 22 from the carry radius to the inspection radius. During inter-station movement, when spring finger assembly 30 is still some distance away from the inspection station, say 4°, a constant amount of positive force is applied by voice coil 56 to move drive roller 54 into position. Just as container 22 is stopping its inter-station movement, drive roller 54 contacts it and begins pushing it radially inward into the inspection station. The carrier disks are still maintaining container 22 at this point, thus during the first portion of segment $t_3$, a small amount of force is preferably applied by the voice coil. Following release of the container by the spring finger assembly, a second portion of segment $t_3$ causes voice coil 56 to exert a greater amount of force against the container, thus causing the container to be moved radially inward at a greater speed. Examples of some parameters used by the algorithm when determining the optimum motion profile of segments $t_1$-$t_3$ include: $_{BOTTLE\_MASS}$, $\tau_{CARRY-INSPEC}$, the inertia of the ARW, the length of the ARW wheel arm, the length of the ARW force arm, the radial distance drive roller 54 must travel, the angular position of the carrier disks which initiates movement of the drive roller, the acceleration rate of the drive roller, and the inertia created during these segments.

Figure 7:
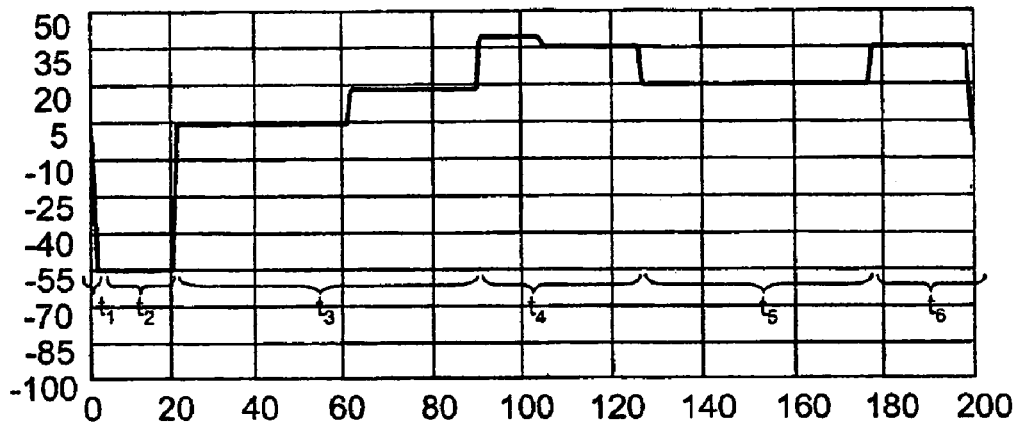
FIG. 7 is a timing chart for an optimum motion profile corresponding to steps 210, 212 and 214 of FIG. 4.

Step 312 involves the calculation of optimum motion profiles for intra-station movement or inspection of container 22 (step 212). This includes optimum motion profiles for both circuit 110 which controls voice coil 56, as well as circuit 112 which controls servo motor 86 (this is the servo motor responsible for rotating the container about its axis). The timing chart for voice coil 56 is shown in FIG. 7 (segments $t_4$-$t_6$), while the timing chart for servo motor 86 is shown in FIG. 8. Starting with the voice coil, in segment $t_4$ the amount of force exerted by the voice coil is sharply increased, thereby compressing and firmly maintaining the container between free-wheeling back-up rollers 52 and drive roller 54. This increase in force, and hence compression of the container, corresponds to a concurrent increase in the rotational acceleration of the container by servo motor 86. Put differently, at the beginning of the inspection process, rotation of the container is quickly accelerated; thus, the drive roller must squeeze the container harder to ensure that the container does not break loose from the rollers. Once the container stops rotationally accelerating (constant rotational velocity), then segment $t_5$ begins.

In segment $t_5$, the amount of force applied by voice coil 56 is lowered to correspond with a constant rotational velocity of the container. This force level maintains constant contact between drive roller 54 and container 22 during inspection. Of course, the pressure exerted by the voice coil could be maintained at the higher lever of segment $t_4$, but that is unnecessary and could wear the bearings out more quickly.

Segment $t_6$ involves a temporary increase of force by the voice coil in order to account for a rotational deceleration of the container, followed by a decrease in the force to zero. During periods of both acceleration and deceleration, the amount of compressive force exerted by the voice coil is increased. Preferably, the force level exerted during deceleration is the same as that exerted during acceleration. Once rotation of the container has been slowed down to an acceptable level, the voice coil reduces the compression on the bottle to zero such that a slight contact is maintained between the drive roller and the container. This slight contact is maintained until the next cycle begins, at which time the drive roller is again retracted, $t_1$. The following parameters are examples of those that can be used by the algorithm for determining optimum motion profiles for segments $t_4$-$t_6$: the inertia of the rotating container. The force is calculated to be proportional to the required force found to work empirically for a given wheel material, bottle diameter, bottle mass and acceleration rate. In essence the equations use this empirical model and calculated a coefficient of friction. Using this calculated coefficient of friction, and a calculated force exerted between the drive wheel and the bottle in the direction of rotation, a new required normal force is calculated to prevent both slip and any bottle motion other than rotational. Turning now to FIG. 8, a timing chart for an optimum motion profile of servo motor 86 is described.

As previously stated, step 312 involves creating optimum motion profiles for both voice coil 56 and servo motor 86. At least two optimum motion profiles must be provided for circuit 112 which drives servo motor 86. One of these profiles is to be used during standard inspection and the other is to be used during mold-code inspection. Referring back to step 304, there is provided a description of the calculations involved for determining the timing chart of FIG. 8. For purposes of brevity, a repeat of that description has been omitted. A similar series of calculations is performed for determining a timing chart for mold-code inspection, if such inspection is to be performed. Examples of parameters that can be used by the algorithm during calculation of optimum motion profiles for servo motor 86 include: the inertia of the rotating container, $\tau_{INTRA-STATION(STD)}$, $\omega_{INSPEC\_START}$, $\tau_{INSPEC\_ACL}$, $\omega_{INSPEC}$, $STANDARD\_RATIO$, $RADIUS\_INSPECTION$ mass of the bottle, and duty cycle of the ARW rotation motor.

Of course many other calculations can and likely would be performed when determining the optimum motion profiles discusses above, as would be apparent to those of ordinary skill in the art. Some of these calculation can include, for example, determining duty cycles for voice coil 56 and servo motors 80-90.

A separate optimum motion profile for moving the container from the inspection radius to the carry radius (step 214) is not needed. At the end of the intra-station segment of operation, the container is still rotating about its axis. At the start of the subsequent intra-station segment, drive roller 54 disengages the container and moves outward, away from the container. The fixed finger assembly 34 is moved into place such that the container spins up the fixed finger assembly, affectively moving the container from the inspection to the carry radius. Accordingly, the operational steps needed to move the container form the inspection to the carry radius are bundled within the other optimum motion profiles.

If steps 300-312 do not violate any of the critical maximums previously established, then a successful set of optimum motion profiles has been created, and the process is complete, step 314. If one or more critical maximums is violated, then the system throughput speed (300 bottles/min) is decreased by a predetermined amount, such as 1 bottle/min, step 316. Afterwards, steps 304-312 are repeated. The algorithm continues this iterative process, preferably using a recursive search algorithm, to develop an optimum motion profile for each of the servo motors 80-90, as well as voice coil 56. Each optimum motion profile should attempt to maximize the throughput speed of apparatus 20, yet obey all of the applicable critical maximums.

Additional Features

In addition to the features explained above, electronic control system 42 is also capable of sensing jams or other malfunctions, and shutting apparatus 20 down in response thereto. Torque limits for servo motors 80-90 are reduced to predetermined levels that cause the servo motors to easily jam if a grossly misshaped or damaged container is received. A jam of a servo motor preferably is sensed by the rotational position sensor of the corresponding driver circuit, which notices when the servo motor is no longer rotating. In response to such a condition, the corresponding driver circuit sends a signal to ECU 100 which alerts the rest of control system 42 of the problem. This in turn shuts indexing and inspection apparatus 20 down and displays trouble-shooting diagnostic information on operator interface 102. Accordingly, this feature acts as a sort of electronic detent rail. It is worth noting that the control system preferably senses the jam by looking for a lack of rotational movement by the servo motor, as opposed to directly monitoring the torque on the servo motor. Alternatively, the control system could sense jams or malfunctions by monitoring torque levels on the various servo motors.

Electronic control system 42 preferably also monitors the operation of apparatus 20 by performing what is referred to as 'station tracking'. Station tracking is performed by making sure that bottles reach each inspection station after each index as anticipated. If a bottle is lost after an inter-station index, then the electronic control system will shut the apparatus 20 down and provide trouble-shooting diagnostic information. In addition to quickly identifying problems, this minimizes the chance of damaging the apparatus. This type of monitoring technique may also be applied to starwheel 72 to make sure that all containers intended for the starwheel make it to that device.

Another feature of the control system of the present invention involves operational feedback. As an example, the distance between infeed device 28 and upper and lower carriers 36, 32 was originally entered with the infeed information in step 200, after it was manually measured. Control system 42 preferably monitors the relationship between the originally entered information and what is being sensed during operation. This relationship between entered and measured information allows the control system to develop an average error that is reported to the operator. The operator is then allowed to modify the information originally entered, which improves the robustness and accuracy of the calculations of step 202. In this way, the control system is constantly monitoring its operation and providing ways for improving it.

The control system of the present invention preferably is also capable of providing scenario reporting. For those occasions where the machine is required to cease operation and exit its normal operational sequence, an exit file is automatically generated that includes information related to the cause of the stoppage. This information can then be retrieved locally or remotely, which allows for remote review of all system parameters during the stoppage. In turn, root cause analysis may be performed offsite, and both troubleshooting and preventative maintenance responses offered to the operator directly through operator interface 102 or other means.

According to another feature of the control system of the present invention, the control system preferably provides remote diagnostics and analysis of the machine during operation. This allows root cause analysis to be performed in real time from a remote location with responses offered to the operator either directly through operator interface 102 or by other means.

The control system also preferably includes a two-way communication link for remote assistance. Within operator interface 102 exists a software mechanism for allowing real time exchange of information between a remote support personnel and the operator at apparatus 20. Along with the previously mentioned remote monitoring devices that are built into the control system, this provides immediate feedback to problems that may arise when operating a complex piece of apparatus in a manufacturing environment.

According to another feature, if the desired container throughput speed set by an operator is less than the container throughput speed obtained by running the optimum motion profiles, then the control system preferably will automatically slow down to the lower speed, thus avoiding unnecessary wear and tear on apparatus 20.

As used in this specification and appended claims, the terms "for example," "for instance," and "such as," and the verbs "comprising," "having," "including," and their other verb forms, when used in conjunction with a listing of one or more components or other items, are each to be construed as open-ended, meaning that that the listing is not to be considered as excluding other, additional components or items. Other terms are to be construed using their broadest reasonable meaning unless they are used in a context that requires a different interpretation.

There have thus been disclosed an indexing and inspection apparatus, an electronic control system, a method for controlling the movement of containers through an apparatus, and a method for determining an optimum motion profile which fully satisfy all of the objects and aims previously set forth. Several alternatives and modifications have been described. Other alternatives and modifications will readily suggest themselves to persons of ordinary skill in the art. The invention is intended to embrace all such alternatives and modifications as fall within the spirit and broad scope of the appended claims.

The invention claimed is:

1. A method for controlling the movement of containers through at least one station of an inspection apparatus, comprising the steps of:
   (a) providing a first servo motor for contributing to inter-station movement of a container,
   (b) providing a second servo motor for contributing to intra-station movement of the container,
   (c) providing an electronic control system for controlling said first and second servo motors,
   (d) inputting information into said control system, said information including at least one physical parameter of the container and at least one critical maximum of the apparatus,
   (e) automatically determining in said control system optimum motion profiles for said first and second servo motors based at least in part on said inputted physical parameter information and said critical maximum information, and
   (f) driving said first and second servo motors according to said optimum motion profiles.

2. The method set forth in claim 1 wherein said inter-station movement comprises a catch sequence, an index sequence and a release sequence.

3. The method set forth in claim 2 wherein said catch sequence causes a first carrier device and a first finger assembly to begin rotating before a second carrier device and a second finger assembly, such that said finger assemblies capture the container therebetween.

4. The method set forth in claim 2 wherein said release sequence causes a first carrier device and a first finger assembly to accelerate away from the container, and a second carrier device and a second finger assembly to stay stationary and in contact with the container.

5. The method set forth in claim 1 wherein said intra-station movement comprises an acceleration sequence, a constant rotational velocity sequence and a deceleration sequence.

6. The method set forth in claim 5 wherein during said intra-station movement said second servo motor causes the container to rotate about its axis and an actuator causes the container to be captured in compression against one or more back-up roller devices.

7. The method set forth in claim 6 wherein said compression is increased during said acceleration and deceleration sequences.

8. The method set forth in claim 6 wherein the amount of said compression is dependent upon said physical parameter inputted during step (d).

9. The method set forth in claim 1 further comprising the step of providing an actuator for moving the container between a carry radius and an inspection radius.

10. The method set forth in claim 9 wherein said actuator begins moving a drive roller while the container is still undergoing inter-station movement.

11. The method set forth in claim 9 wherein said actuator rolls the container along a finger assembly from said carry radius to said inspection radius.

12. The method set forth in claim 9 wherein following said intra-station movement the container is still rotating about its axis, said rotation causes the container to spin along a finger assembly from said inspection radius to said carry radius.

13. The method set forth in claim 1, wherein step (e) further comprises the step of using a recursive algorithm to determine said optimum motion profiles.

14. The method set forth in claim 1 further comprising the step of detecting a container jam or other malfunction by monitoring the rotational position of at least one of said first and second servo motors.

15. The method set forth in claim 1 further comprising the step of station tracking to ensure that containers destined for an inspection station make it to said station.

16. The method set forth in claim 1 further comprising the step of automatically generating an exit file in response to a stoppage of said apparatus, said exit file includes trouble shooting information.

17. The method set forth in claim 1 wherein a plurality of critical maximums are input into the control system and said control system uses a recursive algorithm to determine said optimum motion profiles as a function of said critical maximums and said at least one physical parameter of the container.

18. The method set forth in claim 17 wherein the control system generates a motion profile, tests the generated motion profile to determine if any critical maximum is not satisfied, and alters one or more parameters of that motion profile if an input critical maximum is not satisfied, and then retests the altered motion profile until an optimum motion profile is developed that satisfies all input critical maximums.

19. The method set forth in claim 17 wherein the control system develops a motion profile, tests the generated motion profile and alters one or more parameters of that motion profile until a single critical maximum is determined to be a primary bottleneck whereupon the control system provides additional cycle time to said single critical maximum and retests the motion profile until said single critical maximum is satisfied.

20. The method set forth in claim 19 wherein the control system further develops the motion profile to determine a subsequent critical maximum and alters one or more parameters of the motion profile until testing of the motion profile determines that both said single critical maximum and said subsequent critical maximum are satisfied by a motion profile.

21. The method set forth in claim 20 wherein the control system alters the motion profile and retests the motion profile until all input critical maximums have been satisfied.

* * * * *